(12) United States Patent
Shibata et al.

(10) Patent No.: US 8,238,641 B2
(45) Date of Patent: Aug. 7, 2012

(54) METHOD FOR MEASURING MIRROR INDEX AND APPARATUS THEREOF

(75) Inventors: Kazuhisa Shibata, Himeji (JP); Hiroyuki Ishigaki, Kobe (JP)

(73) Assignee: ARC Harima Co., Ltd., Himeji-shi, Hyogo (JP)

( * ) Notice: Subject to any disclaimer, the term of this patent is extended or adjusted under 35 U.S.C. 154(b) by 1053 days.

(21) Appl. No.: 12/213,590

(22) Filed: Jun. 20, 2008

(65) Prior Publication Data
US 2009/0316959 A1    Dec. 24, 2009

(51) Int. Cl.
*G06K 9/00* (2006.01)
*G01J 3/42* (2006.01)
*G01N 21/47* (2006.01)
*G01B 11/30* (2006.01)

(52) U.S. Cl. ......... 382/141; 356/319; 356/446; 356/603

(58) Field of Classification Search .................. 382/190, 382/141; 356/446, 319, 603
See application file for complete search history.

(56) References Cited

U.S. PATENT DOCUMENTS

| | | | |
|---|---|---|---|
| 4,682,041 A | 7/1987 | Egami et al. | |
| 5,694,197 A * | 12/1997 | Tsukada et al. | 351/206 |
| 6,494,577 B2 * | 12/2002 | Iwanaga | 351/208 |
| 6,974,215 B2 * | 12/2005 | Hayashi | 351/212 |
| 7,027,160 B2 * | 4/2006 | Sperling | 356/446 |
| 7,275,828 B2 * | 10/2007 | Imaizumi | 351/212 |
| 2001/0028440 A1 * | 10/2001 | Iwanaga | 351/208 |
| 2003/0058432 A1 * | 3/2003 | Drake | 356/237.1 |
| 2005/0018136 A1 * | 1/2005 | Hayashi | 351/212 |
| 2005/0195360 A1 * | 9/2005 | Akita et al. | 351/212 |
| 2006/0215176 A1 * | 9/2006 | Van Coppenolle et al. | 356/603 |
| 2008/0024753 A1 * | 1/2008 | Gladnick et al. | 356/3.01 |

FOREIGN PATENT DOCUMENTS
JP    61-75236 A    4/1986

OTHER PUBLICATIONS

Inari, T. "Surface Roughness Measurement by Optical Pattern Projection", Transactions of the Society of Instrument and Control Engineers, 1998, pp. 1539-1545, vol. 34, No. 11, Tokyo, Japan.

* cited by examiner

*Primary Examiner* — Kathleen Y Dulaney
(74) *Attorney, Agent, or Firm* — Smith Patent Office

(57) ABSTRACT

There is provided a method of evaluating quantitatively surface properties such as cleanness and quality of the surface of a work that has been evaluated in the past by visual appearance inspection. A determined pattern 14 is made from plural concentric circles arranged at a center of an object lens in a taking picture device 12. A front edge of a probe is in contact with the surface of a work by the probe 10 that is provided at a middle portion of a cylindrical case 11 in a vertical direction so that the surface of the work and the determined pattern face each other. The determined pattern is illuminated by light of a light source so that a reflected image of the determined pattern is projected onto the surface of the work. A picture of the reflected image is taken by the taking picture device. The resulted image data includes standard deviation of brightness distribution of the resulted image data positioned on radius lines extending in all directions to outside from a center of the ring pattern image. A relative value between the resulted standard deviation and the standard deviation of the amplitude of the brightness distribution of the image data on a plurality of lines of the criteria mirror surface is determined as the mirror index. The image clarity of the surface of the work is evaluated from the mirror index of the plurality of lines.

8 Claims, 8 Drawing Sheets

Imaged picture

Deviation (absolute value)

Deviation (Relative value)

(a)

(b)

(a)

(b)

Imaged picture

Deviation (absolute value)

Deviation (Relative value)

Imaged picture

Deviation (absolute value)

Deviation (Relative value)

Imaged picture

Deviation (absolute value)

Deviation (Relative value)

Imaged picture

Deviation (absolute value)

Deviation (Relative value)

METHOD FOR MEASURING MIRROR INDEX AND APPARATUS THEREOF

TECHNICAL FIELD

The present invention relates to a method of measuring a mirror index that is used to evaluate image clarity on the surface of a work, and more particularly, to a method of evaluating quantitatively surface properties such as cleanness and quality of the surface of a work that has been evaluated in the past by visual appearance inspection.

BACKGROUND ART

For example, how to evaluate the properties of the surface of a work, such as the surface and painted surface of a polished steel plate and the surface of a ceramic product, is very important in product development and merchantability.

For example, even though the surface roughness of a work is low, the surface properties of the work may be evaluated as inferior if the shape of the work is deformed or there is a shape defect. Accordingly, the surface properties of the work can be correctly evaluated by whether the image of the work is accurately projected, that is, image clarity. Image clarity has been evaluated by visual appearance inspection in the past. However, since visual inspection depends on the sense of a human, discriminant criteria are ambiguous, there is the deviation of discrimination caused by personal difference, inspection results are easily affected by ambient environment, and a worker is easily fatigued since it is difficult to continuously perform inspection at high speed even though the inspection is simple. Therefore, there has been a strong demand for the development of a method capable of quantifying image clarity.

Meanwhile, there has been known a method that measures surface roughness, glossiness, or the like as for surface microgeometry and evaluates surface microgeometry from the measured values thereof. However, the surface roughness or glossiness is merely a part of surface properties, and does not correctly reflect the surface properties.

Further, there has been proposed a method that illuminates a pattern plate having slits from the back side thereof by light of a light source, projects the slit pattern onto the surface of a work, and detects the brightness variation of the slit of an image obtained by taking a picture of the pattern, thereby evaluating the finishing level of the surface of the work in stages from the average value or variance of the amplitude of the detection signal (JP-A-61-75236).

Furthermore, the present applicant devised a method that illuminates a determined pattern by light of a light source, projects an reflected image thereof onto the surface of a work, and obtains the standard deviation of the amplitude of the brightness in the brightness distribution of the determined pattern, thereby obtaining the mean roughness Ra of a surface to be measured using a correlationship between the standard deviation and mean roughness Ra of the amplitude that are previously obtained on the same surface. Further, the present applicant filed the application thereof (JP-A-61-75236).

DISCLOSURE OF THE INVENTION

However, since the light passing through the slit is used in the method disclosed in JP-A-61-75236, the profile of the pattern projected onto the surface of the work deteriorates and/or the brightness of color varies due to light diffraction. For this reason, the method cannot be applied to a surface of which the mean roughness Ra is 0.1 µm or more (see "measurement of surface roughness using a projected optical pattern image" written by INARI Takahiko, collected papers of Society of Instrument and Control Engineers collected papers vol. 14 No. 11, 1998 (November, 1998), Society of Instrument and Control Engineers).

Meanwhile, a determined pattern is illuminated and the reflected image thereof is projected onto the surface to be measured in the method disclosed in JP-A-61-75236. The deterioration of the projected pattern caused by light diffraction does not occur and the mean roughness Ra of 0.1 µm or more can also be measured. However, since being simple measurement for obtaining the average value of the mean roughness on the surface of the work, the method is not adequate to accurately evaluate surface properties.

The invention has been made to solve the above-mentioned problems, and an advantage of the invention is to provide a method of evaluating a mirror index that can accurately evaluate surface properties.

According to an aspect of the invention, there is provided a method of measuring mirror index for evaluating image clarity of a surface of work by image analyzing a reflect image of determined pattern being projected onto the surface of work. The method includes providing a space in front of the surface of work to be measured in order to project the determined pattern thereto and taking a picture of the reflecting image of the determined pattern therefrom by positioning a cylinder-shaped hollow probe having an opened front edge so as to face the front edge of the probe in a position of contacted or close to the surface of work to be measured, projecting the determined pattern which includes a ring pattern of one or more parallel circle lines to a surface of work in the space for taking picture, taking a picture of the ring pattern image reflected from the surface of work by means of a taking picture device provided at a rear center of the hollow probe, calculating an amplitude or its standard deviation of brightness distribution of the resulted image data at some points positioned on radius lines extending in all directions at intervals to outside from a center of the ring pattern image, and comparing the resulted amplitude or its standard deviation with a corresponding criterion data previously measured on a criterion mirror surface to determine a relative value as the mirror index.

According to the aspect of the invention, a ring-shaped determined pattern is illuminated, and the reflected image thereof is projected onto the surface of the work, a picture of the reflected image is taken to obtain the amplitude or standard deviation of the brightness distribution of the image data on a plurality of lines extending from the center of the image in the radial direction, and a value relative to the amplitude or standard deviation on the criterion mirror surface is determined as a mirror index, thereby evaluating image clarity from the mirror indexes on the plurality of lines.

Accordingly, for example, if the mirror indexes on the plurality of lines have sufficiently large values and the mirror indexes are the same as each other, it may be determined that there is no anisotropy of the surface roughness, such as the surface roughness is low, the shape of the work is less deformed, or a shape defect is small. Accordingly, an image is accurately and clearly projected onto the surface of the work. As a result, it may be evaluated that the image clarity is high.

Further, if the mirror indexes on the plurality of lines are the same as each other but have small values, it may be estimated that the work does not have the anisotropy of the surface roughness but the surface roughness is large. Furthermore, an image is accurately projected onto the surface of the work but is not clear. As a result, it may be evaluated the image clarity is low.

In addition, if the mirror indexes on the plurality of lines have sufficiently large values and the mirror indexes are the same as each other but have deviation, it may be estimated that the surface roughness is low but the work does not have the anisotropy of the surface roughness. Further, an image is clearly projected onto the surface of the work but is deformed. Even in this case, it may be evaluated that the image clarity is low.

Meanwhile, there are generally many faces having the anisotropy in finish roughness, such as a cutting-finished face, a lapping-finished face, and a buffing-finished face, for example, lathe turning or fraise. However, when the roughness of these faces is measured, measurement is performed in a measuring device capable of performing measurement only in one direction while a measurement direction and a roughness direction are strictly matched to each other. For example, unless measurement is performed in a direction orthogonal to the stripe of the roughness in a contact probe type roughness meter, an error occurs in the measured value. It is not necessarily easy for a user to perform setting while accurately recognizing the stripe of the roughness or the direction orthogonal thereto. This setting error causes the deviation of a measured value.

In contrast, according to the invention, the ring patterns are employed and the roughness is measured on the plurality of lines extending from the center of the ring pattern in the radial direction. Accordingly, a user can perform measurement regardless of the roughness direction.

Further, it is considered that the anisotropy of the surface roughness affects the function or mechanical property of a surface, for example, the beauty of the face, the wetting characteristics of a bonded face, and the composition of contact portions. Therefore, the quantitative comprehension of the anisotropy of the surface roughness is also an important point in measurement. For example, when the anisotropy of the surface roughness is comprehended, measurement needs to be repeatedly performed in the contact probe type roughness meter while the direction is changed, so that large time is required. In contrast, according to the invention, it is possible to instantaneously and quantitatively measure the anisotropy of the surface roughness.

A dedicated mirror may be prepared as the criterion mirror surface, but there is a concern that the dedicated mirror may become lost. It is preferable that opening of the front edge of the cylindrical probe be closed by the cap so that dust does not enter the probe. Accordingly, the inner surface of the cap may be referred to as a criterion mirror surface. A mirror surface, which is formed by depositing aluminum on the surface of a glass and coating the surface of the glass with a protective film and has a reflectivity of 95%, is used as the criterion mirror surface. Further, a usual mirror may be used as the criterion mirror surface.

That is, the cap of which the inner surface is formed of a criterion mirror surface may be fitted to the front edge of the probe so that the criterion mirror surface and the determined pattern face each other, the reflected image of the determined pattern may be projected onto the criterion mirror surface by illuminating the determined pattern by light of a light source, a picture of the reflected image may be taken by the taking picture device, and an amplitude or its standard deviation of brightness distribution of the resulted image data may be calculated at some points positioned on radius lines extending in the radial directions from a center of the ring pattern image.

The standard deviation of the amplitude of the brightness distribution may be calculated on the plurality of lines extending in the radial direction from the center of the ring pattern of the image. The angular intervals are not particularly limited. However, considering that the anisotropy of the surface roughness is one parameter used to evaluate the image clarity, the standard deviation of the amplitude of the brightness distribution may be calculated on the plurality of lines extending at regular angular intervals.

That is, the resulted image data may include standard deviation of brightness distribution of the resulted image data at some points positioned on radius lines extending in all directions at even regular intervals to outside from a center of the ring pattern image.

The determined pattern may be a ring pattern, and the width of the ring is not particularly limited. Further, one or more ring patterns may be provided. In particular, if the determined pattern is a pattern made from plural concentric circles arranged at a center of object lens in the taking picture device, it is possible to evaluate image clarity in a wide range of the surface of the work.

According to another aspect of the invention, there is an apparatus of measuring mirror index for evaluating image clarity of a surface of work by image analyzing a reflect image of determined pattern being projected onto the surface of work. The apparatus includes a cylinder-shaped hollow probe having a front opened edge for providing a space under a condition of shutting out outside in front of the surface of work to be measured in order to project the determined pattern thereto and taking a picture of the reflecting image of the determined pattern therefrom by facing the opened front edge so as to face the front edge of the probe in a position of contacted or close to the surface of work to be measured; a ring body provided with a center opening hole and the determined pattern around the center opening hole, which is attached at an inside periphery of the probe and on which flat face opposite to the surface of work the determined pattern is provided as a ring pattern of one or more plural and parallel concentric circle lines having the same or different widths so as to project the ring pattern on the surface of work; a taking picture device positioned at a rear and center of the hollow probe for taking through the center opening hole the ring pattern image reflected from the surface of work; and a calculating device for obtaining an amplitude or its standard deviation of brightness distribution of the resulted image data outputting from the taking picture device at some points positioned on radius lines extending at intervals to outside from a center of the ring pattern image in all directions, and also comparing the amplitude or its standard deviation with a corresponding criterion data previously measured on a criterion mirror surface to determine a relative value as the mirror index. It is preferable that a cap detachably attached to the front opening edge of the probe be provided at an inside with a criteria mirror face.

The mirror indexes may be evaluated as numerical values that are printed out or displayed on the display. However, since the numerical values need to be compared, it is difficult to intuitively evaluate the numerical values. If an indicating device (display) shows a radial analog-mode indication including a plural of radiuses having a length corresponding to a mirror index on the radius, it is possible to visually evaluate image clarity. Accordingly, it is preferable that the apparatus further include an indicating device showing a radial analog-mode indication comprising a plural of radiuses having a length corresponding to a mirror index on the radius.

In the probe, a taking picture device may be provided in the cylindrical case having an opened front edge, and a determined pattern, which is formed by arranging ring patterns at the center of the object lens in the taking picture device, may be provided at a middle portion of a cylindrical case 11 in a vertical direction. The material and size of the probe are not particularly limited.

The determined pattern may be formed by printing ring patterns on, for example, a film, a sheet, or a plate. Further, the reflected image of the determined pattern is projected onto the criterion mirror surface or the surface of the work, and the determined pattern becomes reference used to calculate a mirror index. For this reason, the flatness is important. Further, if the determined pattern is a pattern indicated on an organic EL or Liquid crystal image indicator, it is possible to appropriately select an appropriate pattern on the surface of the work. Therefore, this is preferable.

Since the determined pattern becomes reference used to calculate a mirror index, the flatness of the determined pattern is important. However, the surface of the work does not necessarily need to be a flat surface. For example, the reason for this is as follows: even if the surface of the work is a cylindrical surface or spherical surface, it is possible to determine whether the cylindrical surface or spherical surface is accurate through the comparison of the mirror indexes on the plurality of lines or the length of the radius thereof.

For example, a computer may be used as the calculating device. Further, various displays, such as a CRT and a liquid crystal display, may be used as the indicating device.

Figure 1:
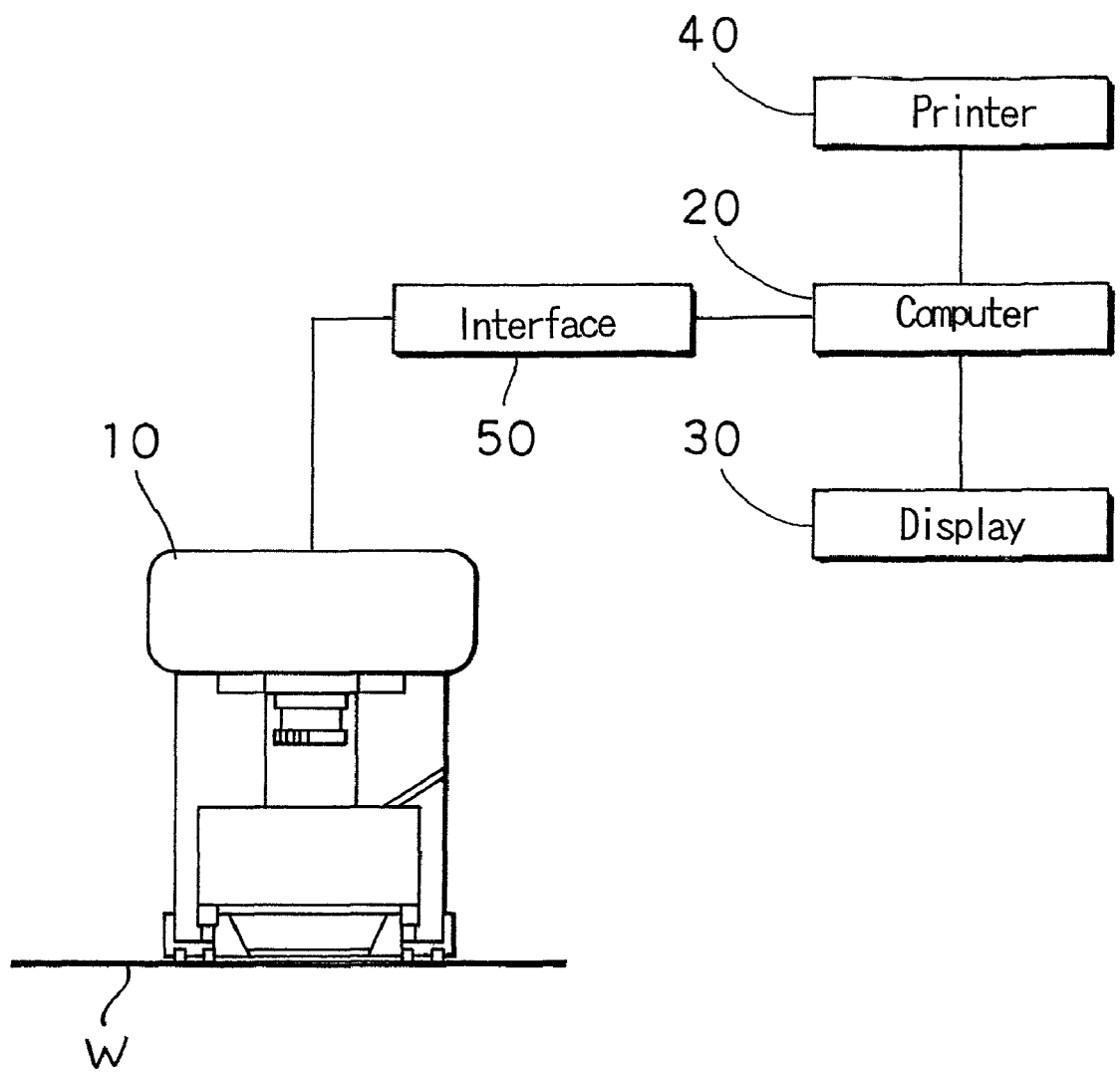
FIG. 1 is a view showing the entire configuration of an apparatus for evaluating image clarity according to a preferred embodiment of the invention.

10 probe
11 cylindrical case
12 CCD camera
14 determined pattern
15 LED (light source)
20 computer (calculating device)
30 display (indicating device)

BEST MODE FOR CARRYING OUT THE INVENTION

The invention will be described in detail below with reference to specific examples shown in drawings. FIGS. 1 to 6 show an apparatus for evaluating image clarity according to a preferred embodiment of the invention. The apparatus according to this embodiment includes a probe 10, a computer (calculating device) 20, a display (indicating device) 30, and a printer 40. The computer 20 is connected to the probe 10 through an interface 50.

Figure 2:
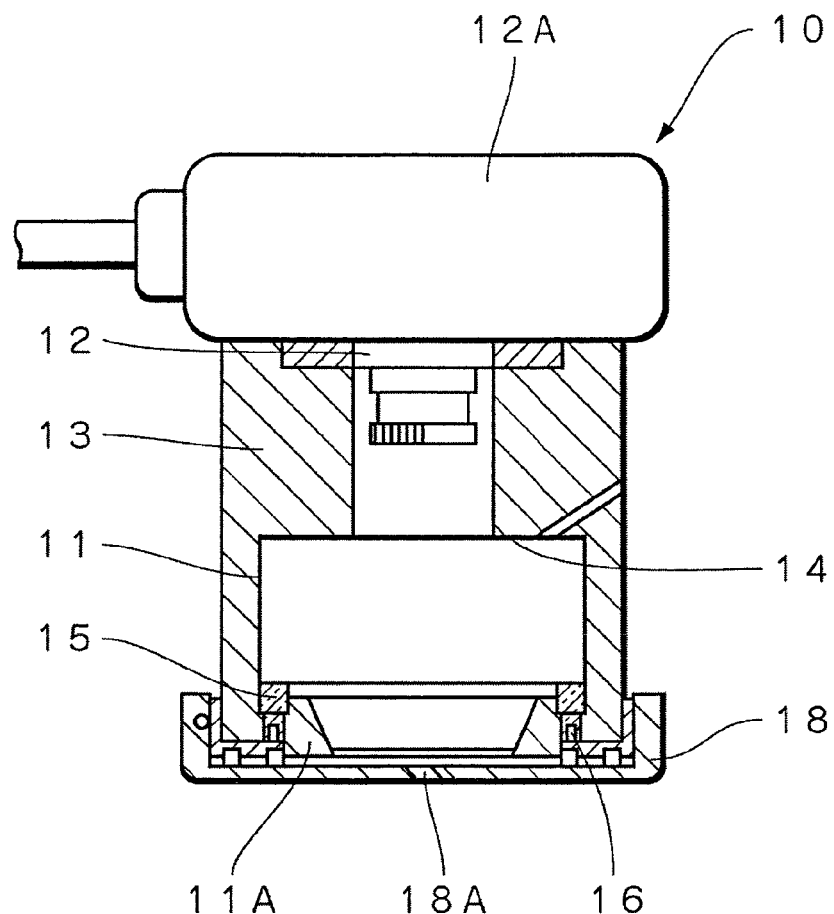
FIG. 2 is a view showing the configuration of a probe of the embodiment.
Figure 3:
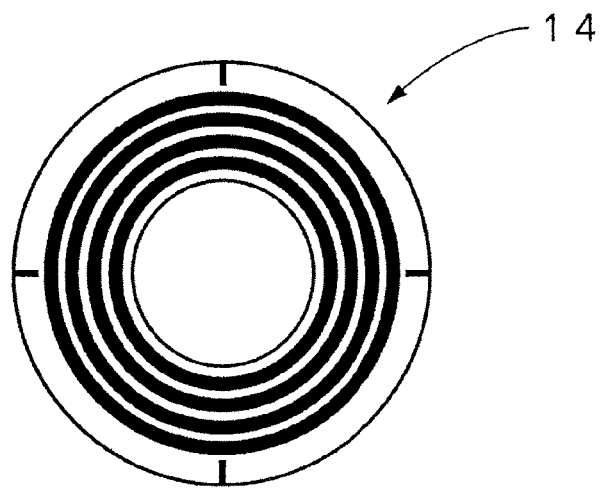
FIG. 3 is a view showing an example of a determined pattern of the embodiment.

As shown in FIG. 2, a case 11 of the probe 10 has a cylindrical shape of which the front edge is opened. A CCD camera 12 is provided in the case 11 so that an object lens faces an opening of the front edge of the case 11, and a signal processing unit 12A for processing a signal of the CCD camera 12 is provided at an upper portion of the case 11.

Further, a cylindrical base 13 is press-fitted into the case 11 of the probe 10, and a determined pattern 14 is provided on the lower end face of the base 13. The determined pattern 14 is formed by forming four ring patterns shown in FIG. 3 on, for example, a ring-shaped film, and the four ring patterns are concentrically laid out at a center of object lens.

In addition, a ring member 11A having a substantially triangular cross section is fitted inside the front edge of the case 11 of the probe 10 and fixed thereto, so that a fitting recess is formed. A plurality of LEDs (light source) 16 is fitted into the fitting recess with a gap therebetween so as to face the determined pattern 14, and a light diffusing ring 15 is fitted to an upper portion thereof.

The light diffusing ring 15 is manufactured by forming fine concavity and convexity on the outer surface of a transparent or translucent plastic ring or dispersing light reflective fine particles or pieces on the inner portion thereof, and disperses light of the LEDs 16 to illuminate the determined pattern 14.

Further, a cap 18 is detachably attached to the front edge of the case 11 of the probe 10, and the inner surface of the cap 18 is formed of a flat criterion mirror surface 18A. In this case, a mirror surface, which is formed by depositing aluminum on the surface of a glass and coating the surface of the glass with a protective film and has a reflectivity of 95%, is used as the criterion mirror surface 18A.

Figure 4:
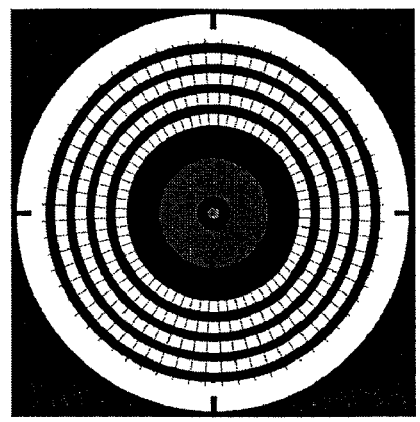
FIG. 4 is a view used to illustrate a method of extracting brightness distribution from image data in the embodiment.
Figure 5:
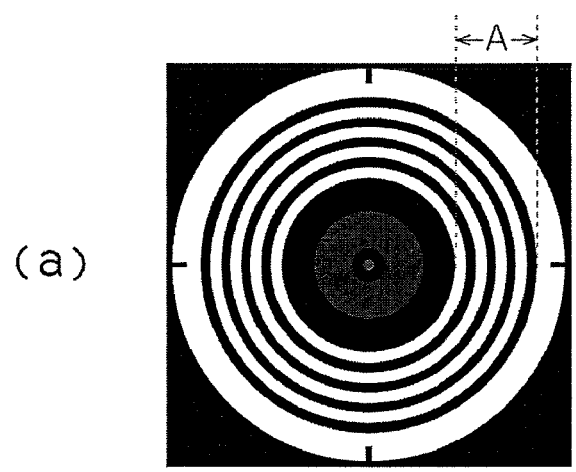
FIG. 5 is a view showing an example of the image data of the embodiment.
Figure 5:
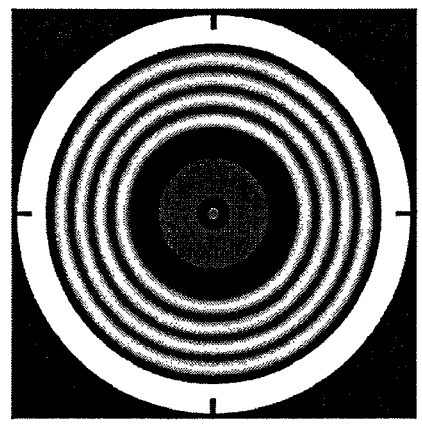
Figure 6:
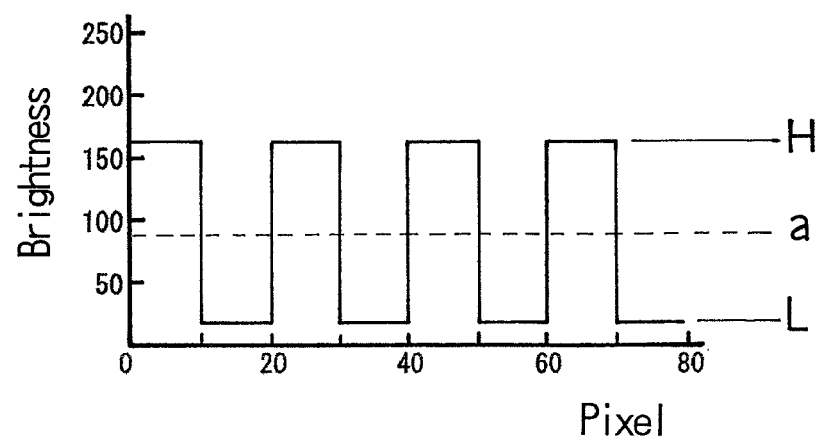
FIG. 6 is a view showing an example of the brightness distribution of the embodiment.
Figure 6:
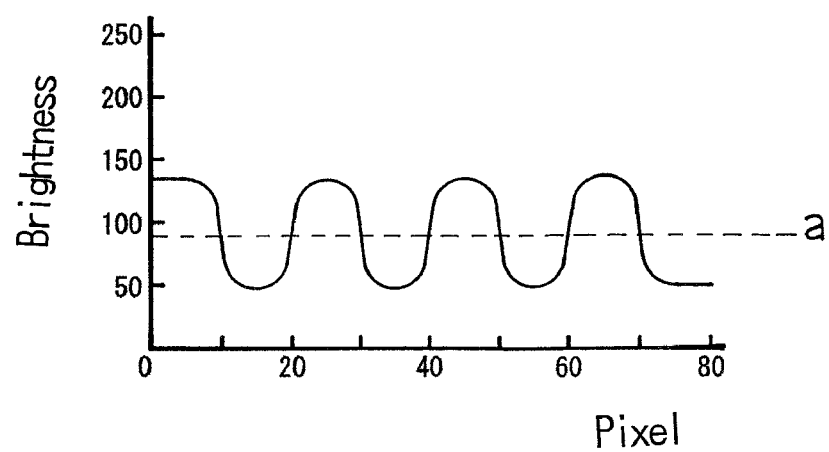

The computer 20 obtains the standard deviation of the amplitude of the brightness distribution of the image data on lines, which extend from the center of a ring pattern of an image obtained on the surface of a work W at regular angular intervals in a radial direction, for example, 64 lines shown in FIG. 4 by using image data from the probe 10 as input. The computer calculates a value relative to the standard deviation, which is previously obtained on the criterion mirror surface 18A, as a mirror index. The computer displays a plurality of mirror indexes, which correspond to the plurality of lines, on the display 30 in accordance with operator's instructions. Further, the computer displays the mirror indexes of the plurality of lines in the form of lines that have a length corresponding to the mirror indexes and extend from the center in the radial direction.

When the image clarity on the surface of the work W is to be evaluated, the probe 10 is operated while the cap 18 covers the case 11 of the probe 10. Then, the light from the LEDs 16 is diffused by the light diffusing ring 15, the determined pattern 14 is uniformly illuminated, the reflected image thereof is formed on the criterion mirror surface of the cap 18, and a picture of the reflected image is taken by the CCD camera 12 and sent to the computer 20.

In the computer 20, the image data of a predetermined range A (see FIG. 5A) of the ring pattern is extracted as data of, for example, 80 pixels, on the 64 lines, which extend from the center of the ring pattern of the image obtained by the computer in the radial direction; the brightness distribution thereof is calculated; and an average value a of the amplitude of the brightness distribution is obtained; standard deviation is calculated from the amplitude and the average value a of a portion L (see FIG. 6A) of the ring pattern and a portion H (see FIG. 6A) between adjacent ring patterns; and the standard deviation of the amplitude of brightness distribution obtained from the 64 lines is stored as the standard deviation of the criterion mirror surface.

After that, the cap 18 is separated, the opening of the front edge of the probe 10 is in contact with the surface of the work W as shown in FIG. 1, the probe 10 is operated so that a picture of the reflected image of the determined pattern 14 projected onto the surface of the work W is taken, and the image data is calculated by the computer 20 like the image data of the criterion mirror surface.

In the case of the surface of the work W, the reflected image of the determined pattern 14 is blurred or changed depending on the roughness or shape anisotropy of the surface of the work W. Accordingly, as shown in FIG. 6B, the shapes of the rising and falling of the brightness distribution of the obtained image data are deformed as compared to the rectangular shapes of the criterion mirror surface 18A, and the amplitude thereof is decreased.

In this case, a relative value between the standard deviation from each of the 64 lines obtained on the surface of the work W and the standard deviation of 64 corresponding lines obtained on the criterion mirror surface 18A is calculated by an expression (standard deviation of surface of work/standard deviation of criterion mirror surface)×reference value (for example, 1000)), and is referred to as a mirror index.

The mirror index, which has been obtained in this way, is stored for each of the 64 lines. If an operator provides instructions to the computer 20 by a key operation or a mouse operation, the mirror index of each of the 64 lines is displayed on the display 30 by a numerical value. Further, if there is an operator's instruction, the numerical value is printed out.

Furthermore, if there is an operator's instruction, the mirror indexes of the 64 lines are displayed on the display 30 by radiuses that have a length corresponding to the 64 mirror indexes and extend in a radial direction.

Since the determined pattern 14 is illuminated by the LEDs 16 and the reflected image thereof is formed on the surface of the work, the reflected image is accurately formed as compared to when a slit pattern is used. Only mean roughness, which is 0.1 μm or less, could be detected in a slit pattern in the related art. In contrast, according to experiments of inventors of the invention, it is possible to detect a surface roughness, which corresponds to a mean roughness of 0.01 to 10 μm, in the method of this embodiment. As a result, it was confirmed that the image clarity could be evaluated at high accuracy. In particular, if the number of the ring patterns of the determined pattern 14 is increased and the profile of the pattern is formed at high accuracy, for example, at a level of μm, it is expected that the image clarity on the surface of the work can be more accurately evaluated.

Figure 7:
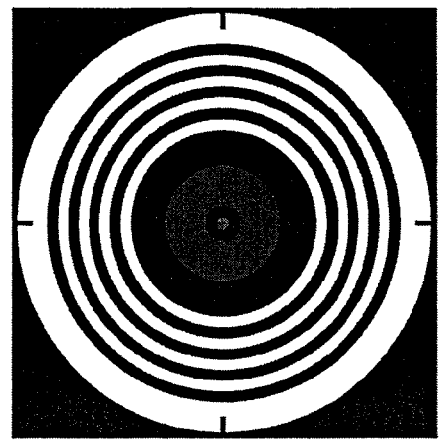
FIG. 7 is a view showing examples of radiuses of a reflected image and a mirror index on the surface of a work.
Figure 7:
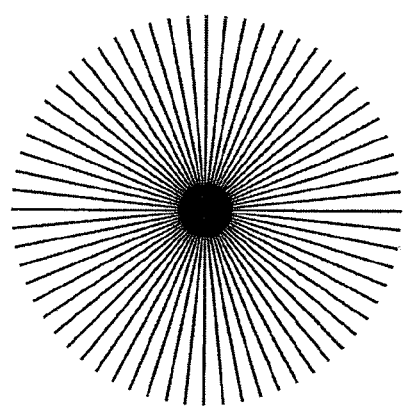
Figure 7:
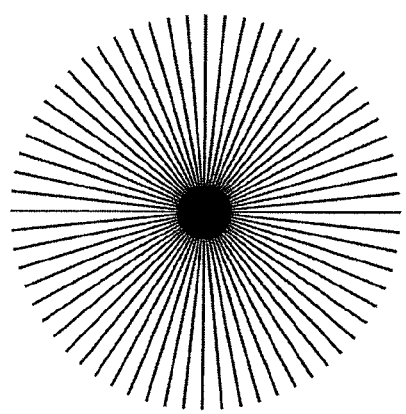

FIGS. 7 to 10 show reflected images of the determined pattern 14 and radiuses (absolute value and relative value) of mirror indexes of other works. FIG. 7 shows a case where the surface roughness of a work is low and the shape anisotropy thereof is low. Since the radiuses of the mirror indexes are sufficiently long and substantially equal to each other, it may be evaluated that the image clarity is high.

Figure 8:
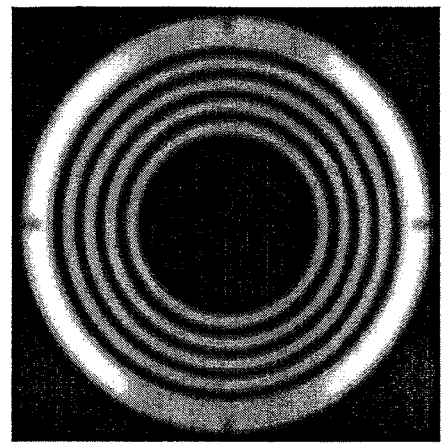
FIG. 8 is a view showing examples of radiuses of a reflected image and a mirror index on the surface of another work.
Figure 8:
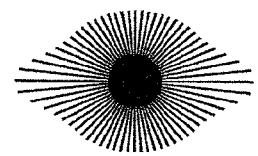
Figure 8:
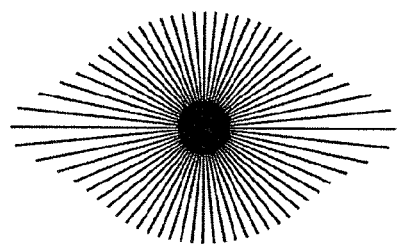

FIG. 8 shows a case where the surface roughness of a work is not too high but the work has shape anisotropy. Since the radiuses of the mirror indexes are not too short but there is the deviation of the lengths of the radiuses, it may be evaluated that the image clarity is not too high.

Figure 9:
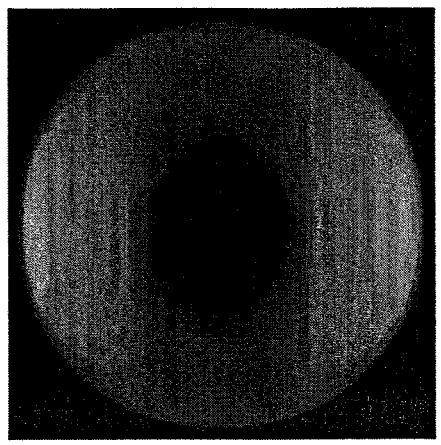
FIG. 9 is a view showing examples of radiuses of a reflected image and a mirror index on the surface of still another work.
Figure 9:
Figure 9:
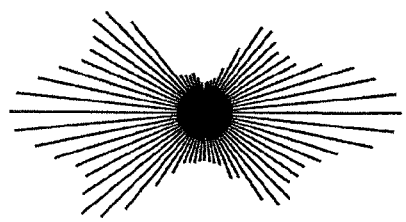

FIG. 9 shows a case where the surface roughness of a work is high and the work has shape anisotropy. Since the radiuses of the mirror indexes are short and there is the deviation of the lengths of the radiuses, it may be evaluated that the image clarity is low.

Figure 10:
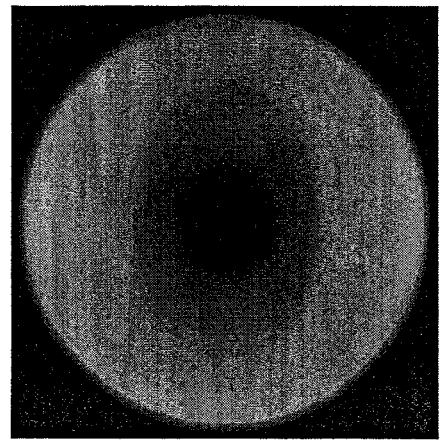
FIG. 10 is a view showing examples of components of a reflected image and a mirror index on the surface of yet still another work.
Figure 10:
Figure 10:
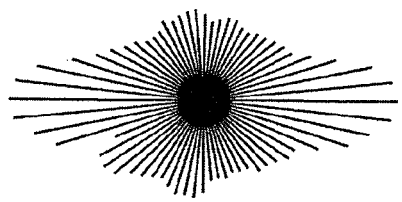

FIG. 10 shows a case where the surface roughness of a work is too high and the work has shape anisotropy. Since the radiuses of the mirror indexes are too short and there is the deviation of the lengths of the radiuses, it may be evaluated that the image clarity is too low.

What is claimed is:

1. A method of measuring mirror index for evaluating image clarity of a surface of work by image analyzing a reflect image of determined pattern being projected onto the surface of work which comprises:

providing a space in front of the surface of work to be measured in order to project the determined pattern thereto and taking a picture of a reflecting image of the determined pattern therefrom by positioning a cylinder-shaped hollow probe having an opened front edge so as to face the front edge of the probe in a position of contacted or close to the surface of work to be measured, projecting the determined pattern which comprises a ring pattern image of one or more parallel circle lines to a surface of work in the space for taking picture, taking a picture of the ring pattern image reflected from the surface of work by means of a taking picture device provided at a rear center of the hollow probe, calculating an amplitude or a standard deviation of a brightness distribution of resulted image data at some points positioned on radius lines extending in all directions at intervals to outside from a center of the ring pattern image, comparing the amplitude or the standard deviation with a corresponding criterion data previously measured on a criterion mirror surface to determine a relative value as the mirror index.

2. A method of measuring mirror index for evaluating image clarity of a surface of work according to claim 1, wherein the criterion mirror surface is provided with a mirror face made from an Al deposited glass face having a reflection rate of 95%.

3. A method of measuring mirror index for evaluating image clarity of a surface of work according to claim 1, wherein the resulted image data comprises standard deviation of brightness distribution of the resulted image data at some points positioned on radius lines extending in all directions at even regular intervals to outside from a center of the ring pattern image.

4. A method of measuring mirror index for evaluating image clarity of a surface of work according to claim 1, wherein the determined pattern is a pattern made from plural concentric circles arranged at a center of object lens in the taking picture device.

5. An apparatus of measuring mirror index for evaluating image clarity of a surface of work by image analyzing a reflect image of determined pattern being projected onto the surface of work which comprises:

a cylinder-shaped hollow probe having a front opened edge for providing a space under a condition of shutting out outside in front of the surface of work to be measured in order to project the determined pattern thereto and taking a picture of a reflecting image of the determined pattern therefrom by facing a opened front edge so as to face the front edge of the probe in a position of contacted or close to the surface of work to be measured, a ring body provided with a center opening hole and the determined pattern around the center opening hole, which is attached at an inside periphery of the probe and on which flat face opposite to the surface of work the determined pattern is provided as a ring pattern image of one or more plural and parallel concentric circle lines having the same or different widths so as to project the ring pattern image on the surface of work, a taking picture device positioned at a rear and center of the hollow probe for taking through the center opening hole the ring pattern image reflected from the surface of work, and a calculating device for obtaining an amplitude or a standard deviation of a brightness distribution of resulted image data outputting from the taking picture device at some points positioned on radius lines extending at intervals to outside from a center of the ring pattern image in all directions, and also comparing the amplitude or the standard deviation with a corresponding criterion data previously measured on a criterion mirror surface to determine a relative value as the mirror index.

6. An apparatus of measuring mirror index for evaluating image clarity of a surface of work according to claim 5, wherein a cap detachably attached to the front opening edge of the probe is provided at an inside with a criteria mirror face.

7. An apparatus of measuring mirror index for evaluating image clarity of a surface of work according to claim 5, further comprises an indicating device showing a radial analog-mode indication comprising a plural of radiuses having a length corresponding to a mirror index on the radius.

8. An apparatus of measuring mirror index for evaluating image clarity of a surface of work according to claim 5, wherein the determined pattern is a pattern indicated on an organic EL or Liquid crystal image indicator.

* * * * *